United States Patent [19]

Grane et al.

[11] 4,273,126
[45] Jun. 16, 1981

[54] ATTACHMENT DEVICE FOR TRACHEAL ASPIRATOR

[75] Inventors: Christian Grane, Kokkedal; Ole B. Kohnke, Kgd. Lyngby, both of Denmark

[73] Assignee: Ruth Lea Hesse, Rungsted Kyst, Denmark

[21] Appl. No.: 875,804

[22] Filed: Feb. 7, 1978

[30] Foreign Application Priority Data

Feb. 8, 1977 [GB] United Kingdom ................. 5218/77

[51] Int. Cl.³ .............................................. A61M 1/00
[52] U.S. Cl. ...................................... 128/276; 433/92
[58] Field of Search ............... 128/276, 277, 281, 300; 15/353, 420, 421; 32/33

[56] References Cited

U.S. PATENT DOCUMENTS

| | | | |
|---|---|---|---|
| Re. 29,321 | 7/1977 | Holbrook | 128/276 |
| 1,202,971 | 10/1916 | Daiber | 128/277 |
| 1,670,610 | 5/1928 | Colby | 128/281 |
| 2,253,143 | 8/1941 | Siegel | 32/33 |
| 3,169,843 | 2/1965 | Campbell | 15/420 |
| 3,343,199 | 9/1967 | Nolte | 15/353 |
| 3,754,554 | 8/1973 | Felbarg | 128/351 |
| 3,965,902 | 6/1976 | Reilly et al. | 128/276 |
| 3,965,903 | 6/1976 | Cranage | 128/276 |

*Primary Examiner*—Robert W. Michell
*Assistant Examiner*—J. L. Kruter
*Attorney, Agent, or Firm*—Spencer & Kaye

[57] ABSTRACT

An attachment device for use in a tracheal aspirator comprising a hand-held container with rigid walls having a secretion inlet opening with an inside diameter sufficiently large to permit passage of solid particles and an outlet opening for connection to the suction tube of a pump. The device further comprises a secretion suction tube of correspondingly large inside diameter and a length just sufficient to enable the device to be operated in front of the mouth of the patient. One end of the suction tube is received by the secretion inlet opening of the container. The inside diameters of the secretion inlet opening and suction tube are between 6 and 12 millimeters and the length of the suction tube is in the range between 200 and 300 millimeters.

12 Claims, 5 Drawing Figures

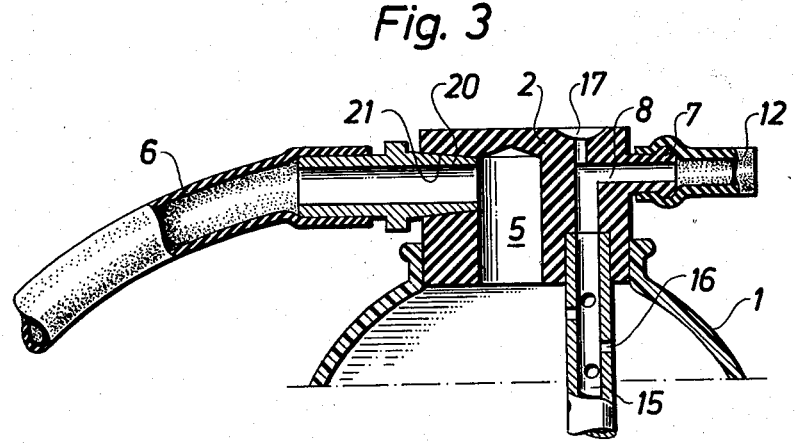
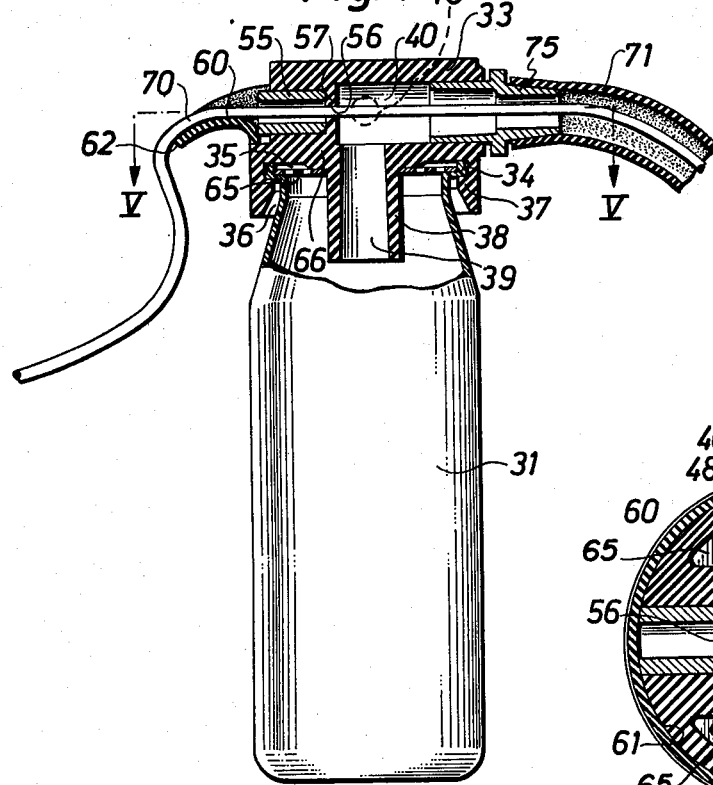
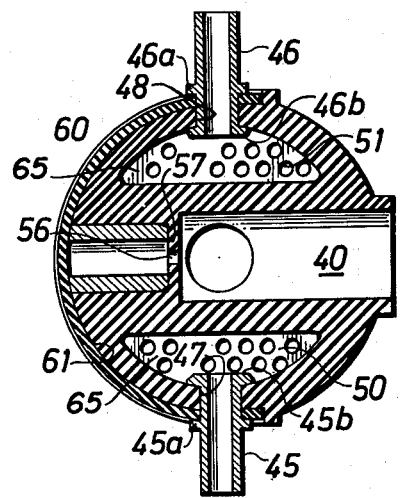

ATTACHMENT DEVICE FOR TRACHEAL ASPIRATOR

BACKGROUND OF THE INVENTION

The invention is concerned with a novel attachment device for use in combination with a pump operating as a tracheal aspirator for sucking and collecting secretion from the oral cavity of an unconscious person and separating large solid particles from the aspired air and from any such liquid secretion as flows to the normal secretion reservoir of the pump.

Tracheal aspirators of the presently used type normally consist of a vacuum pump, the intake opening of which is connected to an airtight collection bottle for aspirated fluid, to which collection bottle a flexible tube is connected. At the end of this tube a tapering suction tip is attached, which can be introduced either directly into the patient's mouth or be connected to a thin extension tube, a so-called suction catheter, capable of being inserted deeper into the airways.

Tracheal aspirators of the type mentioned are all designed with the purpose of effectively removing secretions in liquid or gel form. This purpose is reflected by the fact that the inlet opening of the suction tip inserted into the patient's mouth is designed with a small diameter. This factor permits a high air speed to be obtained at the tip, with only a limited flow of suction air, this high air speed being of decisive importance for the effective drawing-in of material located at some distance from the opening, in cases when the tip cannot be completely submerged in the secretion which is to be removed. On said type of known aspirators the tube connecting the suction tip to the collection bottle is also of relatively small diameter, for the following functional reasons:

(1) The tube must be sufficiently flexible to enable the operator to work the suction tip accurately in the patient's mouth. The larger the diameter, the more unwieldy the tube.

(2) The secretion drawn-in should be transported as quickly as possible to the collection bottle, this being best achieved by a high air speed in the tube, i.e. small diameter. If the tube diameter is too large, some of the secretion will settle and, when pumping ceases, run back out of the suction tip.

When treating victims suffering from respiratory failure, it is often necessary to rapidly remove large quantities of vomitus and blood containing relatively large, solid particles of food and coagulated blood. In aspirators normally used, these particles will be trapped in the suction tip and block the suction. Up to now such particles have had to be scraped out by hand, a both time-wasting and ineffective method.

SUMMARY OF THE INVENTION

The primary purpose of the invention is to produce a collecting device which, when attached to the suction tip of known tracheal aspirators, makes it possible to collect secretion containing large, solid particles and which can quickly be detached when a normal suction tip or suction catheter is to be used for drawing out liquid or mucus.

This purpose is realized by designing an attachment device of the type indicated above so as to comprise a hand-held airtight container with rigid walls having a secretion inlet opening with an inside diameter sufficiently large to permit passage of solid particles normally occurring in secretion such as vomitus, said inlet opening being adapted to receive one end of a secretion suction tube of correspondingly large inside diameter and of a short length just sufficient to enable the device to be operated in front of the mouth of a patient, said container having an outlet opening with means for connecting the device to the suction tube of the pump.

The short suction tube, in spite of the relative stiffness, is easily operated and guided. The large tube dimensions facilitate quick exchange of inlet tubing by using conventional cylindrical or conical connectors.

A secondary field of use of the device is intubation, i.e. introduction of a tube into the trachea, e.g. in connection with narcosis and for artificial ventilation of the lungs with a respirator.

BRIEF DESCRIPTION OF THE DRAWINGS

The invention will now be described in greater detail by reference to the attached drawings showing as non-restrictive examples various embodiments of the attachment device according to the present invention and its component parts. In the drawings:

FIG. 3 shows a slightly modified embodiment of the connecting unit and tube attachment for use in combination with the container according to FIGS. 1 and 2;

FIG. 4 is an elevational view, partly in section, of a second embodiment of the attachment device according to the invention; and FIG. 5 is a transverse section along the line V—V in FIG. 4 of the connecting unit forming part of the embodiment of FIG. 4.

DESCRIPTION OF THE PREFERRED EMBODIMENTS

Figure 1:
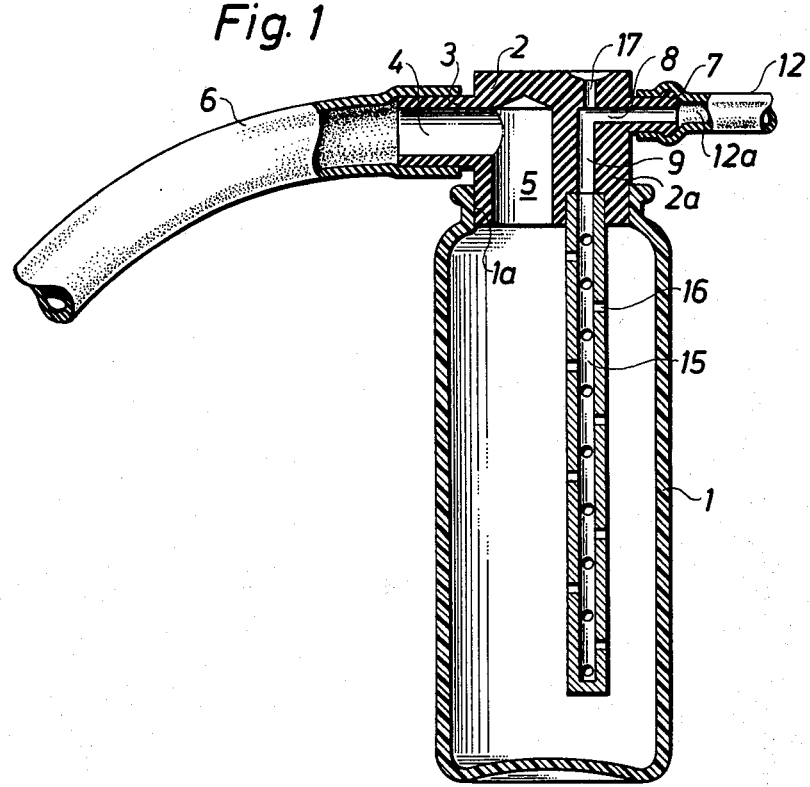
FIG. 1 is a vertical section of one embodiment of the attachment device according to the invention.
Figure 2:
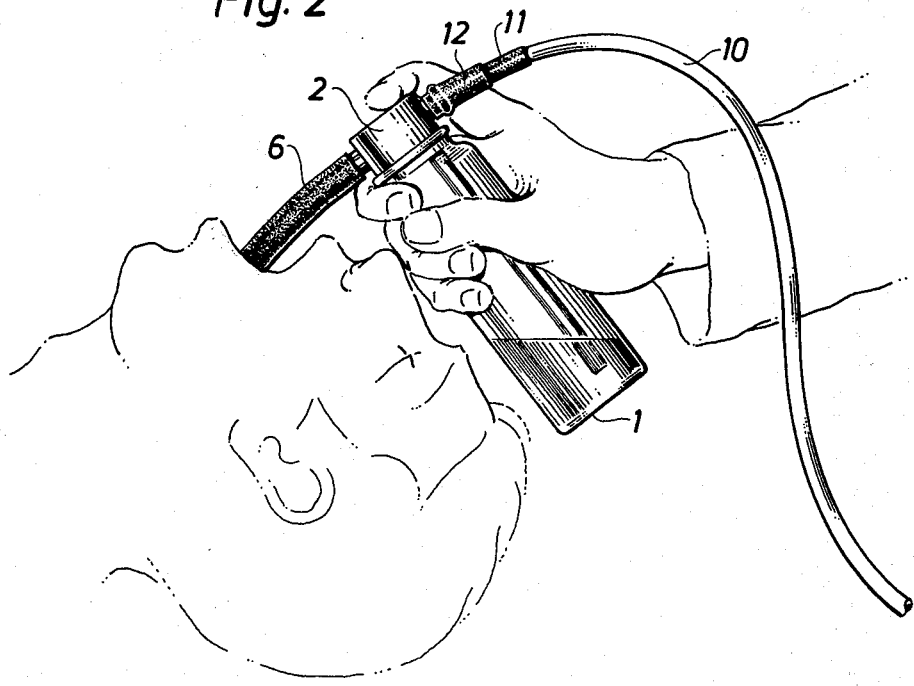
FIG. 2 illustrates the way in which the attachment device is used in practice when attached to the suction tube of a conventional suction pump (not shown)

As shown in FIGS. 1 and 2 an attachment device according to the invention comprises a rigid-walled jar 1 of preferably at least partly transparent material such as plastic, said jar 1 having a diameter permitting the operator to conveniently handle the device by placing his hand around the jar.

The container constituting attachment device in addition to jar 1 comprises a connecting unit 2 having a neck portion 2a sealingly inserted into the neck opening 1a of jar 1. Laterally extending from and integral with the connecting unit 2 is an inlet spout 3 having a large diameter bore 4 communicating with the interior of jar 1 via a duct 5 with large inside diameter. The end of a short secretion suction tube 6 is tightly fitted over the free end of inlet spout 3 to permit the introduction of the free end of tube 6 into the mouth of a patient in a way as illustrated in FIG. 2.

The diameters of both bore 4, duct 5 and tube 6 are chosen in respect to the dimensions of such solid particles, e.g. vomitus and blood coagulations, as normally may occur in the mouth and throat of persons suffering from respiratory failure, e.g. in connection with accidents. The inner diameter of tube 6 may, for example, be 6 to 12 millimeters, a preferred range being 7 to 10 millimeters. The inner diameters of bore 4 and duct 5 may be similar or even slightly larger to avoid obstructions in the transition between bore 4 and duct 5. Tube 6 is made from relatively stiff flexible material and has a length in the range of 200 to 300 millimeters. While the length must be sufficient to enable the free end of the tube to be introduced into the trachea of the patient, it should not exceed the minimum length to an unnecessary extent because manual guiding of the device in the oral cavity and upper air-ducts of the patient is facilitated and suction power is increased by short length.

An outlet spout 7 integral with and laterally extending from the connecting unit 2 opposite the inlet spout 3 has a bore 8 merging into an outlet duct 9 extending through the connecting unit 2 in parallel to inlet duct 5. Bore 8 and duct 9 have considerably smaller dimensions than the corresponding inlet passages because no large-size particles have access to these passages.

Means are provided permitting the suction tips 11 at the free end of the suction tube 10 of a tracheal aspirator of conventional design (not shown) to be attached to the outlet end of outlet spout 7 in communication with bore 8 and duct 9, such means, in the embodiment here described as an example, comprising a sleeve 12 of flexible material sealingly applied around the outside of spout 7 and extending beyond the end of spout 7 thereby exposing a cavity 12a adapted sealingly to receive the suction tip 11 and thereby to put the outlet from jar 1 into communication with the suction side of the tracheal aspirator via suction tube 10.

Inserted into the lower face of connecting unit 2 around outlet duct 9 is a tube 15 of a material offering some resistance to compression and provided with a plurality of perforation 16 having dimensions smaller than the inside diameter of tube 15, thus preventing secretion particles which have been aspired and which are present in jar 1 from sticking and thereby blocking the air flow through tube 8. Together with aspired air, liquid and mucus can pass unhindered through the perforations 16 to be further drawn into the normal collecting bottle of the aspiration suction pump when jar 1 is full of secretion or if the device is used with the connecting unit 2 facing downwards. In any event, liquid and large-sized particles will be separated from each other without causing any interruption of the suction procedure unless both jar 1 and the normal collecting bottle of the tracheal pump are completely filled.

An air relief hole 17 extending from the top of connecting unit 2 into communication with outlet duct 9 and outlet bore 8 enables the operator to remove and re-establish the vacuum in jar 1 and subsequently in the secretion tube 6 by respectively opening and closing hole 17 with a finger-tip in a way appearing from FIG. 2. Alternating between suction and non-suction in this way often serves to relieve partial stoppage in the secretion suction tube. Opening of hole 17 is also effective in immediately removing the vacuum, should the suction opening of tube 6 adhere to the patient's mucous membranes or be introduced into the patient's trachea.

FIG. 3 shows a slightly modified embodiment of the connecting unit 2. In order to accommodate a conically tapering connecting piece 20 attached to the end of suction tube 6, connecting unit 2 in place of the connecting spout 3 of the first embodiment has a correspondingly conically widened inlet bore 21 frictionally receiving the conically tapering end portion of connecting piece 20. By thus providing an easily established and easily relieved, self-locking connection between tube 6 and connecting unit 2 quick removal of the special particle-suction tube 6 and its replacement by a normal endotracheal tube is obtained, such normal endotracheal tubes usually being fitted with standard connections (tapered 1:10 or less) of the type here represented by connecting piece 20. Hereby, valuable seconds, which may be decisive when attempting resuscitation, may be saved, because the doctor is at once able to carry out laryngoscopy and begin to introduce the endotracheal tube which firstly is used in connection with the invention to remove by suction vomitus and blood blocking the way to the trachea. When this has been done, suction is stopped by releasing the finger-tip from hole 17 and the endotracheal tube is introduced into the trachea. Connecting piece 20 is disconnected from tapered bore 21 and a respirator is then attached to connecting piece 20 allowing artificial ventilation of the victim's lungs to start at once.

While it has been stated above that in accordance with the embodiment of FIGS. 1 and 2 and also in the modified embodiment of FIG. 3 inlet and outlet connections are provided on opposite sides of the connecting unit 2, a disposal of the outlet connection in a position at right angles to the inlet connection may have advantages from the operating point of view.

FIGS. 4 and 5 illustrate an embodiment in which the inlet and outlet connections are disposed at right angles to each other and which, in addition, has some complementary features enlarging the field of use of the device and facilitating its operation. In the embodiment according to FIG. 4 the jar 31 is of fundamentally the same type as the jar of the embodiment first described with only a slight modification to be explained later.

In contrast to the embodiment according to FIGS. 1 to 3 the connecting unit 33 is not inserted as a plug into the neck opening of jar 31 but is positioned in resiliently interlocking engagement around a flanged collar 34 bounding the upper end opening of jar 31. For this purpose connecting unit 33 is provided with a lower-end cavity 35 having an outwardly tapering mouth opening 36 facilitating placement of the unit on the open end of jar 31. An undercut circumferential inner edge portion 37 within cavity 35 is located in the position of attachment, underneath the flanged collar portion 34 defining the mouth of jar 31. To enable the connecting unit 33 to be positioned onto jar 31 as shown and to be detached therefrom, connecting unit 33 consists of resilient material such as rubber.

From the bottom of cavity 35 a central projection 38 extends integrally from connecting unit 33 towards the interior of jar 31 in the assembled condition of the attachment device according to FIG. 4. Inlet duct 39 extends through this projection 38 into the interior of connecting unit 33 to a point of intersection with an inlet bore 40 extending at right angles to inlet duct 39 and opening through the side wall of unit 33 as shown in FIGS. 4 and 5. While the entrance portion of bore 40 here is shown as having cylindrical configuration it will be understood that the various configurations of the entrance bore as shown in respectively FIGS. 1, 3 and 5 are interchangable depending on the type of tube connecting elements used.

The transverse sectional view of FIG. 5 illustrates the fact that two alternative outlet connections 45 and 46 are provided in the form of rigid sleeve elements inserted into opposed bores 47 and 48 in the body of connecting unit 33 in about the same plane as inlet bore 40 and each at an angle of about 90° in relation to the inlet bore. Sleeve elements 45 and 46 are provided with suitable central and inner-end flange means 45a, 45b, 46a, 46b enabling sleeve elements 45 and 46 to be anchored in position after insertion from the outside of unit 33 to the position in which flanges 45a, 46a are in abutment with the outer surface of connecting unit 33 and flanges 45b, 46b anchor the inner-ends of sleeve elements 45, 46 within connecting unit 33.

From FIG. 5 it appears that bottom cavity 35 in connecting unit 33 is extended further into connecting unit 33 on both sides of inlet duct 39 and inlet bore 40 to form chambers 50 and 51 each communicating with cavity 35 as well as with one of the outlet connections constituted by sleeve elements 45 and 46. Cavity 35 and chambers 50, 51 together constitute the outlet opening of this embodiment. It will be understood that depending on working conditions the suction tip 11 or other connecting element connecting the device to a conventional tracheal aspirator or similar device may be connected to either sleeve element 45 or 46 while the other one serves as a finger-tip operated vacuum controlling opening.

The disposition of the outlet and inlet openings in the connecting unit 33 as described by reference to FIGS. 4 and 5 not only facilitates handling in general but also permits, for example, alternative left- and right-hand operation of the device.

In practice, there may be cases in which tracheal tubes are used which consist of a comparatively soft, easily flexible material. In such a case the manipulation and guiding of such tubes is performed with the aid of a thin, deformable wire, e.g. of plastic-coated metal, a so-called introduction stylus introduced into the tube and deformed in such a way as to hold and guide the tube as desired. In respect to the attachment of such a soft tube into inlet bore 40 the connecting unit 33 of the embodiment according to FIGS. 4 and 5 is shown provided with means enabling such an introduction stylus to be inserted into the tube during operation of the attachment device. For this purpose a sleeve element 55 is inserted into the body of connecting unit 33 substantially opposite to and in line with inlet bore 40; that is coaxial with bore 40. Communication between the interior of sleeve 55 and the inner end of inlet bore 40 is established through a small hole 56 extending through a thin wall 57 of material left between the bottom of inlet bore 40 and the bottom of the cavity formed within sleeve 55. As no open outlet communication between the inlet ducts of the device and the surrounding atmosphere can be tolerated, the outwardly directed mouth opening of sleeve 55 is closed by a substantially semi-circular rubber strip 60 received in a groove 61 extending around the outer periphery of connecting unit 33 between and slightly beyond sleeves 45 and 46, the central flanges 45a, 46a of sleeves 45 and 46 serving to clamp the rubber strip 60 into a position defined by groove 61 and sealingly covering the mouth opening of sleeve 55.

When the insertion of an introduction stylus 70 is desired, the central portion of rubber strip 60 overlying sleeve 55 is deformed, as shown in FIG. 4, by a downward and outward pulling movement applied to a tab 62 integral with rubber strip 60 and positioned above the mouth of sleeve 55, thereby to expose the mouth opening of sleeve 55 to enable the introduction stylus 70 to be inserted through sleeve 55, hole 56, bore 40 and connecting piece 75 into the soft tube 71 attached to bore 40 to guide this tube and support it in any desired position of deformation. After insertion of the stylus no undesirable communication between inlet bore 40 and the surrounding atmosphere will be left due to the fact that the dimensions of hole 56 will be chosen in such a way as to substantially correspond to the dimensions of the introduction stylus which normally has a diameter within the range of 2 to 5 millimeters.

In contrast to the embodiments according to FIGS. 1 to 3 no extension tube is attached to inlet duct 39. Instead, a perforated, substantially annular particle-retaining strainer element 65 is inserted between the collar-flange portion 34 of jar 31 and the outer wall of projection 38 extending from connecting unit 33 into the mouth of jar 31. Strainer element 65 is held in its position against collar-flange portion 34 by means of shoulders 66 extending downwardly from the bottom of the cavity 35 in connecting unit 33.

In operation the device as shown in FIGS. 4 and 5 will behave exactly as the device previously described by reference to FIGS. 1 and 3.

What I claim is:

1. Attachment device for use in combination with a pump operating as a tracheal aspirator, for sucking and collecting secretion from the oral cavity of an unconscious person and separating large solid particles from the aspired air and from any such liquid secretion as flows to the normal secretion reservoir of the pump, comprising: a hand-held container with rigid walls having a secretion inlet opening with an inside diameter of between 6 and 12 millimeters, said diameter being sufficiently large to permit passage of solid particles normally occurring in secretion such as vomitus; and a secretion suction tube of correspondingly large inside diameter and of a length in the range between 200 and 300 millimeters, said length being just sufficient to enable the device to be operated in front of the mouth of a patient, one end of said tube being received by said inlet opening, said container having an outlet opening provided with means for connecting said device to the suction tube of the pump, a passage being provided substantially in line and in communication with said inlet opening, said passage being normally closed by a lock member adapted to be opened for insertion of an introduction stylus to pass through the inlet opening from the inner end thereof outwardly into the attached secretion suction tube to support said secretion suction tube.

2. Attachment device as claimed in claim 1 in which said inlet opening is cylindrical or conically tapered at a conicity of at most about 1:10 for airtight and self-locking attachment of said secretion suction tube via a complementary cylindrical or conically tapered connector.

3. Attachment device as claimed in claim 1 or 2 further comprising a wall having perforations retaining such normally occurring solid secretion particles separating a receiving space in said container in open communication with said inlet opening from said outlet opening.

4. Attachment device as claimed in claim 3 in which said perforated separating wall is a disk separating the receiving space in said container communicating with said inlet opening from a space within said container communicating with the outlet-opening connecting means.

5. Attachment device as claimed in claim 1 in which said passage constitutes a bushing arranged to substantially sealingly receive such stylus.

6. An attachment device for use with a tracheal aspirator having a vacuum pump and connection bottle, said attachment device separating large solid particles from the secretion collected from the oral cavity of a person while permitting the liquid in said secretion to flow through said attachment device to said collection bottle, said attachment device comprising:

a hand-held open end jar for collecting said secretion;
a connecting unit sealingly coupled to the mouth of said jar, said connecting unit including
  inlet means having a bore with a diameter of between 6 and 12 millimeters to permit secretion including large solid particles to pass therethrough,
  an inlet duct connecting the bore of said inlet means with the interior of said jar,
  an outlet means having a passage of smaller diameter than that of the bore of said inlet means connecting said outlet means to the interior of said jar, and
  a flanged collar surrounding the open end of said jar and defining a cavity connecting the interior of said jar to said outlet means;
a perforated particle-retaining element located within said cavity interposed between said jar and said outlet means, the perforations in said particle-retaining element being small enough to prevent the large solid particles in said secretion to pass therethrough while permitting the liquid therein to be sucked into said outlet means;
a secretion suction tube connected to said inlet means for insertion into the oral cavity of a person, the inner diameter of said secretion suction tube being substantially the same as that of the bore of said inlet means and the length of said secretion suction tube being between 200 and 300 millimeters; and
a connecting suction tube for coupling said outlet means to the collection bottle of said tracheal aspirator, said connecting suction tube being of smaller diameter than said secretion suction tube.

7. An attachment device as claimed in claim 6 which further comprises an aperture in said connection unit for connecting the interior of said jar to the atmosphere, the sucking action of said attachment device being controllable by covering and uncovering said aperture.

8. An attachment device as claimed in claim 6 wherein said particle-retaining element is a perforated disc.

9. Attachment device for use in combination with a pump operating as a tracheal aspirator, for sucking and collecting secretion from the oral cavity of an unconscious person and separating large solid particles from the aspired air and from any such liquid secretion as flows to the normal secretion reservoir of the pump, comprising:

a hand-held container with rigid walls comprising a container jar and a closure member sealingly attachable to said container jar to form said container, said closure member having a secretion inlet opening, an outlet opening and two air ducts extending through said closure member to provide communication between the interior of said container and the ambient atmosphere, said air ducts being symmetrically located on either side of said inlet opening, the inside diameter of said secretion inlet opening being between 6 and 12 millimeters to permit passage of solid particles normally occurring in secretion such as vomitus;
a secretion suction tube attachable to said inlet opening, said suction tube having a diameter corresponding to that of said secretion inlet opening and a length in the range between 200 and 300 millimeters, said length being just sufficient to enable the device to be operated in front of the mouth of a patient; and
means for connecting one of said air ducts to the suction reservoir of said pump, the other air duct opening outwardly in a position enabling the user holding said container to respectively cover and uncover it with a fingertip to control the state of vacuum within said container and thereby the suction action.

10. Attachment device as claimed in claim 9 in which said inlet opening is cylindrical or conically tapered at a conicity of at most about 1:10 for airtight and self-locking attachment of said secretion suction tube via a complementary cylindrical or conically tapered connector.

11. An attachment device for use with a tracheal aspirator having a vacuum pump and connection bottle, said attachment device separating large solid particles from the secretion collected from the oral cavity of a person while permitting the liquid in said secretion to flow through said attachment device to said collection bottle, said attachment device comprising:

a hand-held open end jar for collecting said secretion;
a connecting unit sealingly coupled to the mouth of said jar, said connecting unit including
  inlet means having a bore with a diameter of between 6 and 12 millimeters to permit secretion including large solid particles to pass therethrough,
  an inlet duct connecting the bore of said inlet means with the interior of said jar, and
  an outlet means having a passage of smaller diameter than that of the bore of said inlet means connecting said outlet means to the interior of said jar, said outlet means comprising two elements substantially coplanar with said inlet means, the elements comprising said outlet means projecting in opposite directions from said connecting unit and each being substantially perpendicular to said inlet means;
a perforated particle-retaining element interposed between said jar and said outlet means, the perforations in said particle-retaining element being small enough to prevent the large solid particles in said secretion to pass therethrough while permitting the liquid therein to be sucked into said outlet means;
a secretion suction tube connected to said inlet means for insertion into the oral cavity of a person, the inner diameter of said secretion suction tube being substantially the same as that of the bore of said inlet means and the length of said secretion suction tube being between 200 and 300 millimeters; and
a connecting suction tube for coupling said outlet means to the collection bottle of said tracheal aspirator, said connecting suction tube being of smaller diameter than said secretion suction tube.

12. An attachment device for use with a tracheal aspirator having a vacuum pump and connection bottle, said attachment device separating large solid particles from the secretion collected from the oral cavity of a person while permitting the liquid in said secretion to flow through said attachment device to said collection bottle, said attachment device comprising:

a hand-held open end jar for collecting said secretion;
a connecting unit sealingly coupled to the mouth of said jar, said connecting unit including
  inlet means having a bore with a diameter of between 6 and 12 millimeters to permit secretion including large solid particles to pass therethrough, an inlet duct connecting the bore of said inlet means with the interior of said jar, and an outlet means having a passage of smaller diameter than that of the bore of said inlet means connecting said outlet means to the interior of said jar;

a perforated particle-retaining element interposed between said jar and said outlet means, the perforations in said particle-retaining element being small enough to prevent the large solid particles in said secretion to pass therethrough while permitting the liquid therein to be sucked into said outlet means;

a secretion suction tube connected to said inlet means for insertion into the oral cavity of a person, the inner diameter of said secretion suction tube being substantially the same as that of the bore of said inlet means and the length of said secretion suction tube being between 200 and 300 millimeters, a further passage being provided coaxial with said inlet means for insertion of an introduction stylus to support said secretion suction tube, sealing means secured to said connecting unit for permitting insertion of said stylus and also for sealing said further passage both before and after said stylus has been inserted therein; and a connecting suction tube for coupling said outlet means to the collection bottle of said tracheal aspirator, said connecting suction tube being of smaller diameter than said secretion suction tube.

* * * * *